United States Patent

Cohen-Laroque

[11] Patent Number: 6,120,443
[45] Date of Patent: Sep. 19, 2000

[54] DEVICE FOR DETERMINING THE DEPTH OF ANESTHESIA

[76] Inventor: Emmanuel-S. Cohen-Laroque, Les Pommeraies, F - 74160 Archamps, France

[21] Appl. No.: 09/155,891
[22] PCT Filed: Apr. 8, 1997
[86] PCT No.: PCT/IB97/00363
    § 371 Date: Oct. 7, 1998
    § 102(e) Date: Oct. 7, 1998
[87] PCT Pub. No.: WO97/37586
    PCT Pub. Date: Oct. 16, 1997

[30] Foreign Application Priority Data

Apr. 9, 1996 [FR] France ................................ 96 04547

[51] Int. Cl.[7] ........................................................ A61B 5/00
[52] U.S. Cl. ............................................. 600/300; 128/897
[58] Field of Search ........................ 600/300; 128/897–98

[56] References Cited

U.S. PATENT DOCUMENTS 3,946,725  3/1976  Bolshov et al. .

FOREIGN PATENT DOCUMENTS 0 232 234 A2  8/1987  European Pat. Off. .
24 30 788     6/1974  Germany .
WO 92/06632   4/1992  WIPO .

*Primary Examiner*—John P. Lacyk
*Attorney, Agent, or Firm*—Davis and Bujold

[57] ABSTRACT

A method comprising a step (10) of acquiring a patient heart activity signal, a signal shaping step (11) comprising a step (19) of converting the analog signal into a digital signal, a step (12) of sensing a periodic wave in the signal, a step (13) of calculating time intervals between the periodic waves, a step (14) of determining digital time interval series, a step (15) of calculating a fractal dimension of the digital series, and a step (16) of calculating the depth of anesthesia on the basis of the fractal dimension.

28 Claims, 4 Drawing Sheets

DEVICE FOR DETERMINING THE DEPTH OF ANESTHESIA

BACKGROUND OF THE INVENTION

The present invention concerns a method and a device for determining the depth of anesthesia in a patient to whom at least one anesthetic substance has been administered.

It is essential to measure the depth of anesthesia administered to a patient as precisely and objectively as possible for two reasons: first, to determine the optimal analgesic and amnesiac effects of the anesthetic agent and second, to minimize the risks of anesthesia.

Optimal conditions can be attained only if the depth of anesthesia can be precisely and objectively evaluated.

Several methods and devices presently exist which determine, to some extent, the depth of anesthesia in a patient. In most cases the anesthetist determines the depth of anesthesia empirically based on exterior symptoms of pain in the patient such as a sweaty forehead, excretion of tears, ocular myosis, or an extreme reaction of the cardiovascular system such as tachycardia or bradycardia, abnormal blood pressure, etc. However, since these parameters vary from patient to patient, evaluating the depth of anesthesia may depend heavily on the subjective judgment of the anesthetist.

One method of determining the depth of anesthesia is proposed in International Patent Publication No. WO 91/19453. This method involves repeatedly administering stimuli to the patient, recording the patient's electrical brain activity after each stimulus, processing the data electronically, and transforming the resulting data into indications of the depth of anesthesia. Since this method involves administering stimuli to the patient, it may not always be practical. Furthermore, such a response is independent of the patient's autonomous nervous system and does not take into account the instant state of the autonomous nervous system.

Another method and apparatus designed to furnish measurements of the depth of anesthesia in a patient are described in International Patent Publication No. WO 92/06632. In this method, a series of waves R is analyzed statistically to plot the modifications in cardiac frequency variations caused by respiration. The instant frequency is compared to an average frequency in order to quantify the depth of anesthesia.

In actuality, this method is generally useless if the patient is artificially ventilated during surgery. In this situation, physiological control of ventilation has no influence on the mechanics of respiration.

SUMMARY OF THE INVENTION

The present invention proposes a method which determines the depth of anesthesia in real time, individually for each patient, based on the reactivity of the independent nervous system and without resorting to any subjective criteria. It also proposes a relatively simple apparatus for determining the depth of anesthesia in real time.

This object is achieved by a method such as that defined in the preamble, characterized in that it comprises a step of acquiring at least one signal representing the patient's cardiac activity, a step of detecting the position of a periodic wave determined for each of the patient's cardiac signals, a step of calculating the time intervals between said periodic waves, a step of determining series of digital time intervals, a step of calculating a fractal dimension for said series of time intervals, and a step of determining the depth of anesthesia as a function of the fractal dimension.

According to various embodiments of the invention, the step of acquiring at least one signal may consist of measuring either the patient's electrocardiogram, blood flow velocity, blood light absorption factor, blood pressure, oxygen content of the blood, or the acoustical signal emitted by the heart.

According to another variation, it is also possible to elect to measure at least two of the following parameters: electrocardiogram, blood flow velocity, blood light absorption factor, blood pressure, oxygen content of the blood, or the acoustical signal emitted by the heart.

According to a preferred embodiment, said periodic wave corresponds to an electrocardiogram wave R.

According to an advantageous embodiment, the method further comprises a step of configuring the signals representing the patient's cardiac activity, a step of converting said signals into digital signals, and a step of filtering said digital signals.

The step of detecting the position of a periodic wave determined for each signal of the patient's heart preferably consists of calculating a coefficient of correlation between the signal representing the cardiac activity in the patient and a theoretical model of said periodic wave, and then determining the extrema of the coefficient of correlation.

The step of determining digital series of time intervals advantageously consists of calculating the time interval between two consecutive extrema with the same type of coefficient of correlation and forming series comprising a given number of time intervals.

The given number of time intervals in a digital series preferably ranges from to 10 80.

The step of determining a fractal dimension for said series of time intervals advantageously consists of calculating a dimension of correlation for said series.

According to a preferred embodiment, the step of calculating the depth of anesthesia as a function of the fractal dimension consists of determining the fractal dimension of the series of digital time intervals before administering at least one anesthetic substance to the patient, defining a coefficient of normalization such that the product of this coefficient and the fractal dimension are essentially equal to a reference value, and multiplying the fractal dimension of the series of time intervals after administration of at least one anesthetic substance to the patient, by the coefficient of normalization.

According to one advantageous embodiment, an alarm signals when the depth of anesthesia has surpassed a predetermined threshold.

According to a preferred embodiment, the arithmetic mean of several fractal dimensions is calculated, said mean being used to calculate the depth of anesthesia.

According to another preferred embodiment, one depth of anesthesia is calculated for each signal of cardiac activity by the patient and a mean of the anesthesia depths obtained for each signal is used.

It is also possible to use a variation or a correlation of the anesthesia depths obtained for each signal.

The goal of the present invention is also achieved by a device such as that described in the preamble, characterized in that it comprises means for acquiring at least one signal representing the patient's cardiac activity, means for configuring said signal, means for detecting periodic waves determined for each such signal, means for calculating the temporal position of said periodic waves, means for measuring the time intervals between said periodic waves, means for forming digital series containing a given number of time intervals, means for calculating a fractal dimension for said digital series, means for calculating a coefficient of normalization, and means for displaying the depth of anesthesia.

According to a preferred embodiment, the signal configuration means comprises an operational amplifier which maintains the voltage of each signal between two predetermined limits and an analog/digital converter which samples the signal generated by the amplifier at a given sampling frequency.

The sampling frequency is advantageously higher than 500 Hz.

According to a preferred embodiment, the means for detecting periodic waves consists of a microprocessor which calculates the coefficient of correlation between each signal representing cardiac activity by the patient and a theoretical model of said predetermined periodic wave.

The device of the present invention preferably has a memory device for recording the point at which the coefficient of correlation reaches an extremum.

According to an advantageous embodiment, the device comprises an alarm which signals when the depth of anesthesia surpasses a predetermined threshold.

According to a preferred embodiment, the device includes a means for regulating the measurement parameters.

Said regulating means may include a means for regulating the number of time intervals in each digital series and/or a means for regulating the threshold value beyond which the alarm will signal.

The means for displaying anesthesia depth advantageously consists of a liquid crystal display screen.

BRIEF DESCRIPTION OF THE DRAWINGS

The advantages of the present invention will be more apparent with reference to the following description of one preferred embodiment and the attached drawings, wherein:

FIG. 5b is a schematic drawing of the exterior of the device of FIG. 5a.

DESCRIPTION OF THE PREFERRED EMBODIMENTS

Figure 1:
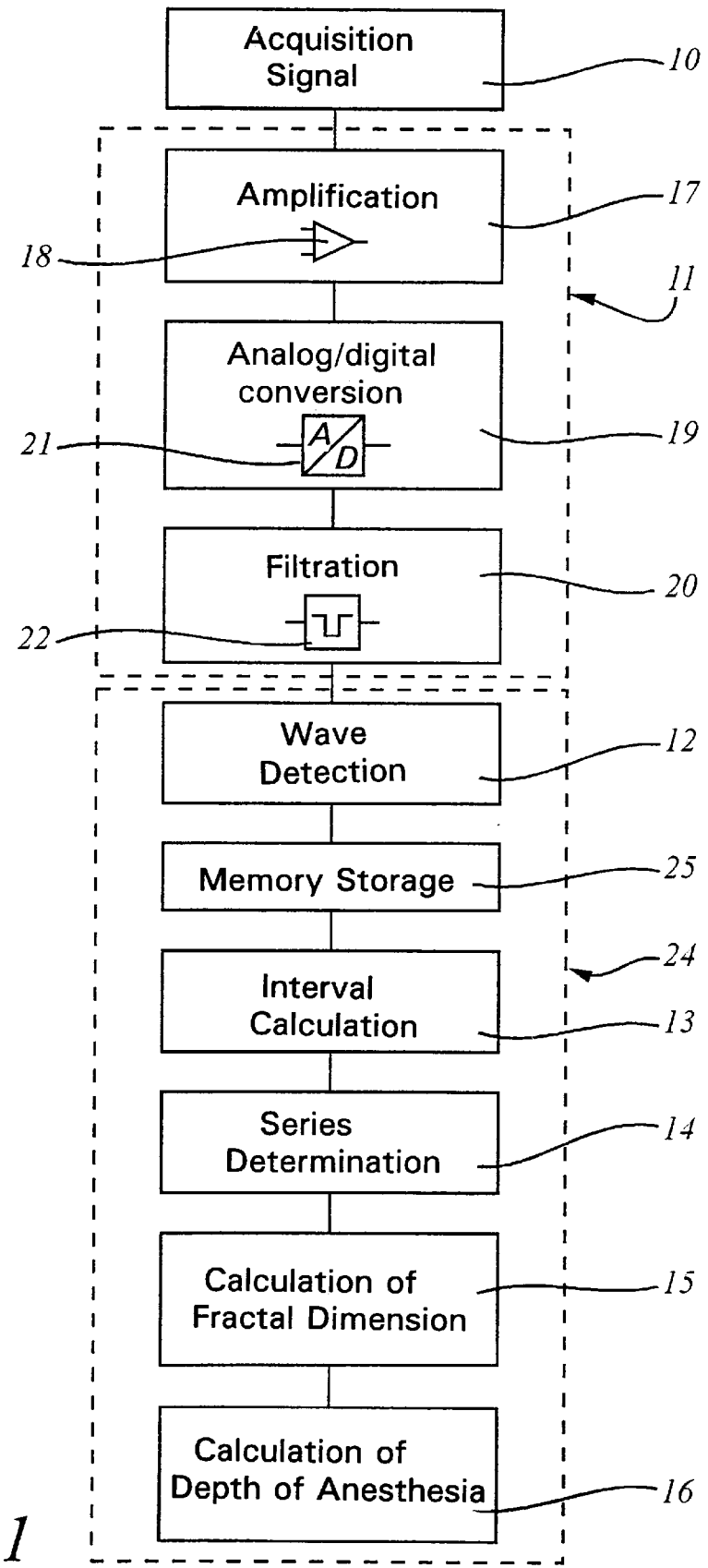
FIG. 1 is a block schematic drawing of the method of the present invention.

The method of the present invention is described below with reference to FIGS. 1 through 4. This method essentially consists of a step 10 of acquiring a signal representing the patient's cardiac activity, a step 11 of configuring said signal, a step 12 of detecting a periodic wave such as, for example, wave R, in the configured signal, a step 13 of calculating the time intervals between said successive periodic waves, a step 14 of determining digital series of time intervals, a step 15 of calculating a fractal dimension for said series of time intervals, and a step 16 of calculating the depth of anesthesia as a function of the fractal dimension.

Step 10, acquiring the signal representing the patient's cardiac activity, is performed in a manner known in the art. The signal may originate from an electrocardiograph, for example. Other signals can be used, especially a signal representing the patient's blood flow velocity, blood light absorption factor, blood pressure, oxygen content of the blood, or sound waves emitted by the heart.

Electrocardiographs currently in use deliver an analog electrical signal with a voltage that ranges from −1V to +1V, from −5V to +5V, or from −10V to +10V. The configuration 11 of such a signal comprises a normalization step 17 which consists of amplifying the signal using an operational amplifier 18 so that the resulting signal may range from between −5V to 5V, for example, whatever type of electrocardiograph is used. The return from this operational amplifier 18 can be automatically modified as a function of the amplitude of the input signal. This configuration also includes a step 19 of converting said analog signal into a digital signal, and a step 20 of filtering said digital signal.

Conversion step 19 consists of introducing the output signal of amplifier 18 into an analog/digital converter 21 which samples the signal at a sampling frequency higher than 500 Hz and, for example, at a frequency ranging from 500 Hz to 2 kHz. Sampling resolution may be higher than 8 bits and may equal 13 bits, for example. Filtration step 20 consists of introducing the signal into a conventional filter 22 in order to eliminate a component with a frequency corresponding to the frequency of the electrical power supply.

Figure 2:
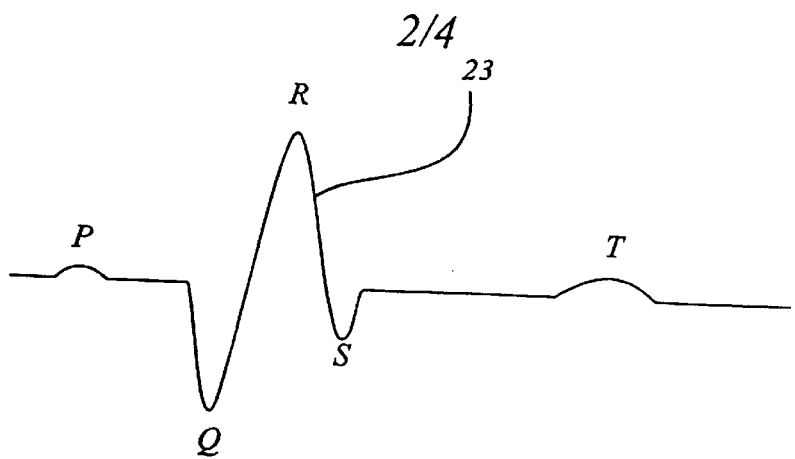
FIG. 2 is a theoretical model of an electric cardiac diagram as a function of time.

FIG. 2 shows a theoretical model of the signal generated by an electrocardiograph. This signal has one zone with a strong positive amplitude, known to a person skilled in the art as wave R, referenced as number 23 in FIG. 2. Step 12 of the method of the present invention consists of detecting the position in time of these waves R 23. This detection is accomplished using a method known by the name "digital matched filtering", which consists of calculating the maximum correlation function of two signals. One of these signals is the sampled signal originating from filter 22 and the other signal is a theoretical signal representing wave R. This method consists of separating "theoretical" wave R from the actual signal and measuring the correlation as a function of separation. This correlation is expressed mathematically as follows:

$$\varphi_{xy}(k) = \sum_{l=0}^{N-1} x(l-k)y(l)$$

where x is the actual signal from the filter, y is the theoretical signal, l corresponds to the sample number of the sampled signal and N is the number of samplings from the sampled signals.

This calculation is performed using a micro-processor 24 which may be, for example, a microprocessor manufactured by Texas Instruments known by the name Digital Signal Processing TMS 320 C25.

The value 1 corresponding to the maximum correlation function $\phi_{xy}$ indicates the position of wave R in time. This value is stored in the storage device 25 associated with microprocessor 24. This calculation is repeated in order to detect the position of all waves R as a function of time.

Figure 3:
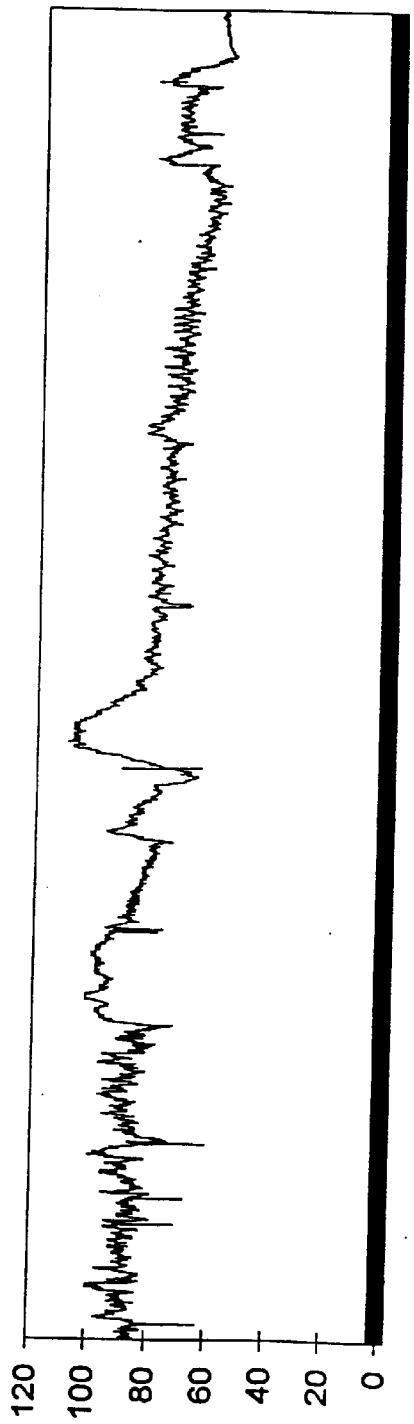
FIG. 3 is an example of an experimental diagram of intervals between the waves R of a patient as a function of time.

Step 13 consists of calculating the time interval separating two successive waves R. All these calculated intervals are stored in storage device 25. The graph illustrated in FIG. 3 shows the intervals R—R as a function of time.

In step 14 these intervals are next regrouped to form digital series comprising a certain number of intervals R—R. Stated concretely, the larger the number of intervals R—R used to constitute a digital series, the higher the precision and reliability of the measurement. However, as the number of intervals increases, the waiting period between variations in the depth of the patient's anesthesia and the display of these variations by the apparatus also becomes longer. Therefore, a compromise must be found between these two limitations. In actuality, a series ranging from 20 to 80 intervals, preferably about 40 intervals, produces reliable, quick results.

The next phase consists of determining the depth of anesthesia as a function of the information concerning the digital series of intervals R—R.

Cardiac pulsations are generated by the heart and regulated by a certain number of parameters specifically associated with the autonomic nervous system. The number of parameters is directly linked to the fractal dimension of a digital series of intervals R—R. Administering one or more types of anesthesia to a patient modifies the number of parameters regulating cardiac function and consequently, the fractal dimension of the series of intervals R—R corresponding to the patient's heartbeat. Calculating the fractal dimension, therefore, provides a measurement of the depth of anesthesia.

Step 15 consists of calculating the fractal dimension of each digital series of intervals R—R. This fractal dimension can be approximated by determining a dimension of correlation for the digital series. This dimension of correlation can be calculated using the following formula:

$$D = \lim_{r \to 0} \frac{\log C(r)}{\log r}$$

where C(r) is the sum of correlation.

Step 16 consists of transforming this correlation dimension into data representing the depth of anesthesia. In order to adapt the method to each individual patient, the correlation dimension is determined before the anesthetic is injected. The mean value for several correlation dimensions obtained for a given patient before injection is multiplied by a coefficient of normalization such that the product corresponds approximately to an arbitrary given value, for example, 100 units.

The depth of anesthesia thus equals the dimension of correlation for a series of digital intervals R—R or for an average dimension of correlation, multiplied by the coefficient of normalization defined above. In actuality, it may be advantageous to calculate an average dimension of correlation or an average depth of anesthesia in order to obtain a more stable value. Generally, the average is calculated based on from two to ten series. However, it is also possible to use only one series for each calculation. It is also possible to use one variation or one correlation of several series.

Figure 4:
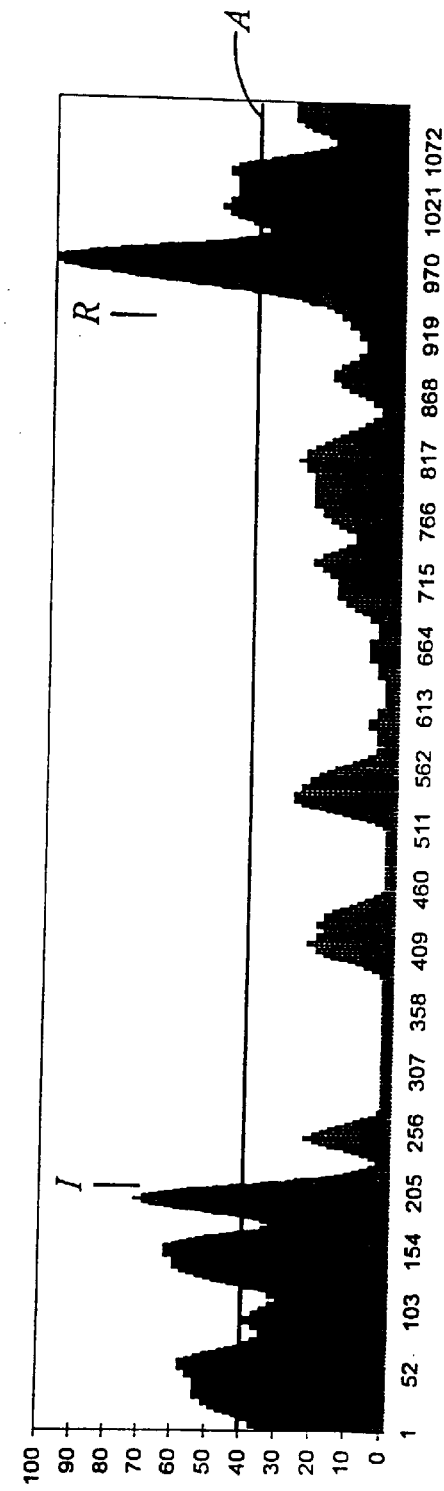
FIG. 4 is a diagram of the dimension of correlation in the diagram of FIG. 3.

FIG. 4 uses histograms to show the depth of anesthesia of a patient as deduced from the graph of FIG. 3. The portion of this drawing to the left of the vertical line, identified as 1, represents the depth of anesthesia before injection of the anesthetic. Line 1 represents injection of the anesthesia. The vertical line denoted by R represents the patient awakening, and the area between lines 1 and R represents the period during which the anesthesia is active. Horizontal line A represents a threshold value which the depth anesthesia should not exceed during the period of anesthesia, that is, between 1 and R.

Certain parameters of the method of the invention may be modified to adapt the response and sensitivity of the apparatus to the patient being treated and the procedures performed. More specifically, these parameters are the size of the temporal series (number of intervals R—R) used when calculating the correlation dimension, and the number of correlation dimensions used to calculate the average depth of anesthesia. It is also possible to perform other statistical calculations such as fluctuations, standard deviations, type of divergence, etc.

Using the method of the present invention, it is also possible to fix the threshold value of the depth of anesthesia corresponding to horizontal line A of FIG. 4. If the depth of anesthesia exceeds this value, an alarm alerts the anesthetist that the patient is beginning to awaken. It may then be necessary to readminister anesthesia. In FIG. 4, this threshold value is fixed at 40 units. It is determined for each patient by the anesthetist.

Figure 5A:
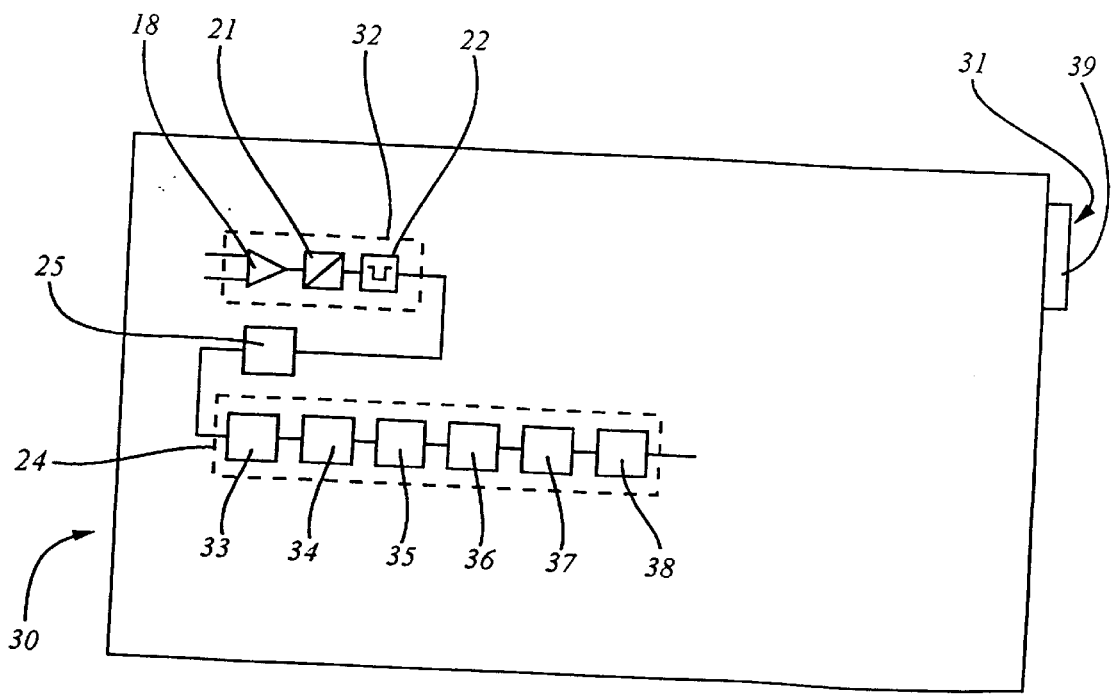
FIG. 5a is a schematic drawing of the interior of the device of the present invention.
Figure 5B:
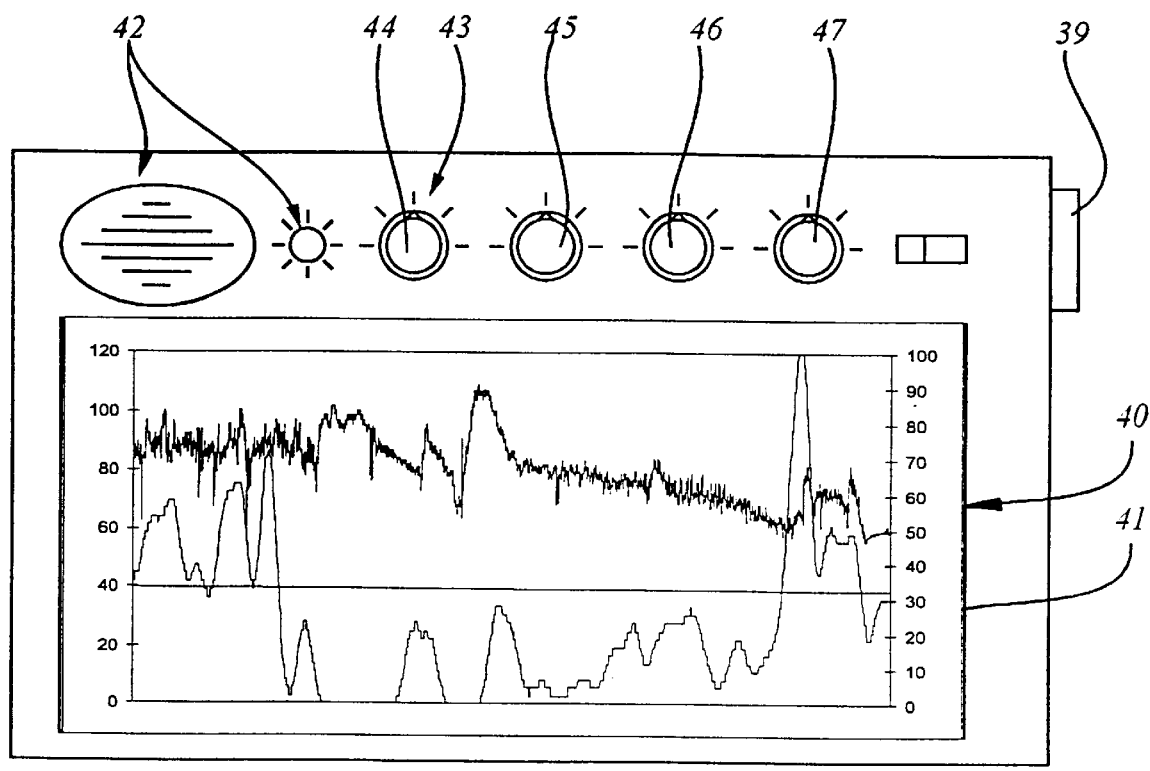

The device 30 of the present invention is described with reference to FIGS. 5a and 5b. The device consists essentially of a means 31 for acquiring at least one signal representing the patient's cardiac activity, a means 32 for configuring each signal, a means 33 for detecting periodic waves, a means 34 for calculating the temporal position of said periodic waves, a means 35 for measuring the intervals, a means 36 for forming digital series, a means 37 for calculating a fractal dimension, and a means 38 for calculating a coefficient of normalization. Elements 33 through 38, as well as data storage device 25, may all consist of microprocessor 24.

Acquisition means 31 comprises a connector 39 for connecting device 30 to the output of an electrocardiograph, for example. Element 32 for configuring the signal consists of the operational amplifier 18, the analog/digital converter 21, and the filter 22. The amplifier normalizes the maximum amplitude of the electrocardiograph output signal, so that this amplitude always ranges between the same two limits, whatever the maximum amplitude of the electrocardiograph output. The analog/digital converter samples the signal coming from the amplifier, and the filter eliminates parasitic frequencies, particularly frequencies originating from the main electrical supply.

Device 30 also includes a display means 40 showing the depth of anesthesia, which may consist, for example, of a liquid crystal display screen 41. The display means makes the various data immediately accessible. The information which is always displayed on the screen is the correlation dimension. This information might be displayed in the form of histograms as a function of time, as shown in FIGS. 4 and 5b. Another useful piece of information is the value of each interval R—R as a function of time. A change in the correlation dimension might be caused by a change in the patient's anesthetized state, in which case it would be necessary to react by administering additional anesthesia; but it could also be caused by a destabilizing factor such as a pulmonary obstruction or hemorrhage, for example. In this case the reaction would be not be the same. Because the screen displays intervals R—R and the depth of anesthesia simultaneously, the anesthetist is able to instantaneously evaluate the depth of anesthesia in the patient and any changes in that state. It is also possible to display a line showing the depth of anesthesia beyond which an alarm will sound, allowing the anesthetist to easily evaluate the disparity between the instant depth of anesthesia and critical depth, and thereby anticipate changes in the patient's condition.

Device 30 also incorporates an audio and/or visual alarm 42 activated when the depth of anesthesia in the patient surpasses a predefined threshold value.

Finally, device 30 includes a means 43 for regulating the measurement parameters. This consists of a regulatory device 44 for selecting the number of intervals R—R per series, and a regulatory device 45 for choosing the number of interval series R—R used for each display of the correlation dimension. In practice, the higher the number of series, the more stable the value, but the greater the delay in detecting changes in the patient's condition. The number of series used generally ranges from 1 to 10.

Regulatory means 43 also comprises a means 46 for regulating the coefficient of normalization between the correlation dimension and the depth of anesthesia. This coefficient of normalization may be regulated either manually, by adjusting the potentiometer, or automatically using device 30.

Regulatory means 43 also includes a means 47 for regulating the alarm level so that the anesthesia depth which will trigger the alarm can be adjusted. The anesthetist determines this adjustment based on the risks presented by the patient and what phase of surgery is in process.

Electricity may be supplied to the device of the invention through the main power supply when it is used in the operating room, or by a battery if it is removed from the operating room to the recovery room.

A primary advantage of this method and device is that they provide an objective evaluation of the depth of anesthesia. The administration of anesthesia can be very precisely calibrated, reducing the cost of the pharmaceutical agent used and decreasing the risks associated with anesthesia. The possibility of precisely evaluating the depth of anesthesia means that new anesthetic agents can be tested with greater reliability and objectivity. Moreover, the functions of the patient's autonomic nervous system can be precisely and objectively analyzed.

Since the device of the present invention is not directly connected to the patient, the norms of medical protection are more flexible and greatly simplified. The device is compact enough to be installed quickly on standard monitoring equipment.

Using this device, the anesthetist is able to react quickly to any change in the depth of the patient's anesthesia, before the first signs of distress are apparent. Since it is well known that the better a patient withstands anesthesia, the better the recovery, the device also helps to reduce post-surgical complications.

The present invention is not limited to the embodiment described. It is possible to use signals other than the output signal of an electrocardiograph. In particular, if surgery is performed on the thorax, an electrocardiogram cannot be measured. In this case, a measurement would be taken of the patient's blood pressure, blood flow velocity based on the Doppler effect, or some other related parameter, such as light absorption, oxygen content in the blood, or acoustical cardiac signals. It is also possible to measure several of these parameters, calculate a depth of anesthesia for each, and combine these depths of anesthesia. This produces a more reliable result and greater safety during anesthesia.

What is claimed is:

1. A method for determining a depth of anesthesia of a patient to whom at least one anesthetic drug was administered, the method comprising the steps of:

firstly, acquiring (10) a plurality of successive signals representing a cardiac activity of the patient;

secondly, detecting (12) a periodic wave determined for the plurality of successive signals representing the cardiac activity of the patient;

thirdly, calculating (13) time intervals between successive periodic waves;

fourthly, determining (14) a digital series of the time intervals;

fifthly, calculating (15) a fractal dimension of the determined digital series of the time intervals; and sixthly, calculating (16) a depth of anesthesia of the patient as a function of the fractal dimension.

2. A method according to claim 1, wherein the step of acquiring (10) a plurality of successive signals representing the cardiac activity of the patient comprises the step of measuring an electrocardiogram of the patient.

3. A method according to claim 1, wherein the step of acquiring (10) a plurality of successive signals representing the cardiac activity of the patient comprises the step of measuring a blood flow velocity of the patient.

4. A method according to claim 1, wherein the step of acquiring (10) a plurality of successive signals representing the cardiac activity of the patient comprises the step of measuring a light absorption factor of blood of the patient.

5. A method according to claim 1, wherein the step of acquiring (10) a plurality of successive signals representing the cardiac activity of the patient comprises the step of measuring a blood pressure of the patient.

6. A method according to claim 1, wherein the step of acquiring (10) a plurality of successive signals representing the cardiac activity of the patient comprises the step of measuring an oxygen content of blood of the patient.

7. A method according to claim 1, wherein the step of acquiring (10) a plurality of successive signals representing the cardiac activity of the patient comprises the step of measuring an acoustic signal emitted by a heart of the patient.

8. A method according to claim 1, wherein the step of acquiring (10) a plurality of successive signals representing the cardiac activity of the patient comprises the step of measuring at least two of the following parameters:

an electrocardiogram of the patient;

a blood flow velocity of the patient;

a light absorption factor of blood of the patient;

a blood pressure of the patient;

an oxygen content of blood of the patient; and an acoustical signal emitted by a heart of the patient.

9. A method according to claim 2, further comprising the step of detecting an electrocardiogram wave R (23) as the periodic wave determined for each signal of the cardiac activity of the patient.

10. A method according to claim 1, further comprising the steps of:

configuring the acquired plurality of successive signals representing the cardiac activity of the patient;

converting (19) the plurality of successive signals representing the cardiac activity of the patient into digital signals; and filtering (20) the converted digital signals prior to the step of determining the periodic wave for the plurality of successive signals representing the cardiac activity of the patient.

11. A method according to claim 1, wherein the step of determining (12) the periodic wave for the plurality of successive signals representing the cardiac activity of the patient further comprises the step of calculating a correlation coefficient between the signal representing the cardiac activity of the patient and a theoretical model of the periodic wave, and determining the extrema of the correlation coefficient.

12. A method according to claim 11, wherein the step of determining (14) the digital series of the time intervals comprises the step of calculating a time interval between two consecutive extrema having a same type of correlation coefficient, and forming a series of a given number of time intervals.

13. A method according to claim 12, further comprising the step of using a number ranging from 10 to 80 as the series of the given number of time intervals.

14. A method according to claim 1, wherein the step of calculating (15) the fractal dimension of the determined digital series of the time intervals comprises the step of calculating a dimension of correlation for the determined digital series of the time intervals.

15. A method according to claim 1, wherein the step of calculating (16) the depth of anesthesia of the patient as a function of the fractal dimension comprises the steps of determining the fractal dimension of the digital series of the time intervals before administration of at least one anesthetic substance to the patient, defining a coefficient of normalization such that a product of the coefficient and the fractal dimension are essentially equal to a reference value; and multiplying the fractal dimension of the series of the time intervals, after the administration of the at least one anesthetic substance to the patient, by the coefficient of normalization.

16. A method according to claim 13, further comprising the step of activating an alarm when the depth of anesthesia exceeds a predetermined threshold value.

17. A method according to claim 1, further comprising the step of calculating an arithmetic mean of several fractal dimensions, and using the arithmetic mean to calculate the depth of anesthesia.

18. A method according to claim 8, further comprising the step of calculating a depth of anesthesia for each signal representing the cardiac activity of the patient, and using a mean value of the depth of anesthesia obtained for each signal.

19. A device for determining a depth of anesthesia in a patient to whom at least one anesthetic substance was administered, the device comprising:

means (31) for acquiring a plurality of signals representing the cardiac activity of the patient;

means (32) for configuring the plurality of signals representing a cardiac activity of the patient;

means (33) for determining periodic waves for each of the configured plurality of signals representing the cardiac activity of the patient;

means (34) for calculating a temporal position of the determined periodic waves;

means (35) for measuring time intervals between the determined periodic waves;

means (36) for forming a digital series containing a given number of time intervals;

means (37) for calculating a fractal dimension for the digital series;

means (38) for calculating a coefficient of normalization and calculating a depth of anesthesia as a function of the fractal dimension; and means (40) for displaying the depth of anesthesia.

20. A device according to claim 19, wherein the means (32) for configuring the plurality of signals comprises an operational amplifier (18) which maintains a voltage of each signal between two predetermined limits, and an analog/digital converter (21), coupled to the operational amplifier (18), which samples the signal coming from the amplifier at a given sampling frequency.

21. A device according to claim 20, wherein the sampling frequency is greater than 500 Hz.

22. A device according to claim 19, wherein the means (33) for determining periodic waves comprises a microprocessor (24) which calculates a correlation coefficient between the signal representing the cardiac activity in the patient and a theoretical model of a predetermined periodic wave.

23. A device according to claim 22, wherein the device is coupled to a storage device (25) for recording instances when the correlation coefficient attains an extremum.

24. A device according to claim 19, wherein the device is coupled to an alarm device (42) which produces a signal when the depth of anesthesia surpasses a predetermined threshold level.

25. A device according to claim 19, wherein the device further comprises means (43) for regulating measurement parameters.

26. A device according to claim 25, wherein the means (43) for regulating measurement parameters further comprises a device (44) for regulating a number of time intervals in each digital series.

27. A device according to claim 25, wherein the means (43) for regulating measurement parameters further comprises a device (47) for regulating a threshold value above which a alarm signal is emitted.

28. A device according to claim 19, wherein the means (40) for displaying the depth of anesthesia comprises a liquid crystal display screen (41).

* * * * *